(12) United States Patent
Schneider et al.

(10) Patent No.: US 11,678,814 B2
(45) Date of Patent: Jun. 20, 2023

(54) MOUTHPIECE, SYSTEM AND METHOD FOR ENABLING A MEASUREMENT OF ANALYTES IN EXHALED AIR

(71) Applicant: Robert Bosch GmbH, Stuttgart (DE)

(72) Inventors: Stefan Schneider, Beilstein (DE); Markus Thuersam, Weil Der Stadt (DE); Frank Barth, Tamm (DE); Tom Doehring, Stuttgart (DE); Klaus Mueller, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 792 days.

(21) Appl. No.: 16/621,976

(22) PCT Filed: Jun. 1, 2018

(86) PCT No.: PCT/EP2018/064474
§ 371 (c)(1),
(2) Date: Dec. 12, 2019

(87) PCT Pub. No.: WO2018/228832
PCT Pub. Date: Dec. 20, 2018

(65) Prior Publication Data
US 2021/0298636 A1   Sep. 30, 2021

(30) Foreign Application Priority Data
Jun. 13, 2017   (DE) .................... 10 2017 209 909.7

(51) Int. Cl.
*A61B 5/08*   (2006.01)
*A61B 5/097*   (2006.01)

(52) U.S. Cl.
CPC .............. *A61B 5/082* (2013.01); *A61B 5/097* (2013.01); *A61B 2562/0247* (2013.01)

(58) Field of Classification Search
None
See application file for complete search history.

(56) References Cited

U.S. PATENT DOCUMENTS

| | | | |
|---|---|---|---|
| 9,643,186 B1 | 5/2017 | Ahmad et al. | |
| 2014/0024960 A1* | 1/2014 | Smith | A61B 5/082 |
| | | | 600/543 |

FOREIGN PATENT DOCUMENTS

| | | |
|---|---|---|
| CN | 101454040 A | 6/2009 |
| CN | 104105443 A | 10/2014 |
| | (Continued) | |

OTHER PUBLICATIONS

International Search Report corresponding to PCT Application No. PCT/EP2018/064474, dated Aug. 24, 2018 (German and English language document) (5 pages).

*Primary Examiner* — Jay B Shah
(74) *Attorney, Agent, or Firm* — Maginot, Moore & Beck LLP

(57) ABSTRACT

A mouthpiece for a device for measuring analytes in exhaled air includes a gas path configured to convey exhaled air to the device and a film arranged so as to block the conveying of the exhaled air through the gas path. A system, in one embodiment, includes the mouthpiece and a device configured to measure analytes in the exhaled air. The mouthpiece is configured to be releasably connected to the device. The device includes a pressure sensor and, in one embodiment, a pump configured to pump air via the mouthpiece when connected to the device. The device is configured to be enabled to measure predefined analytes in the exhaled air when a pressure curve measured via the pressure sensor satisfies one or more predefined conditions.

20 Claims, 3 Drawing Sheets

(56) References Cited

FOREIGN PATENT DOCUMENTS

| | | |
|---|---|---|
| CN | 105339486 A | 2/2016 |
| CN | 105722460 A | 6/2016 |
| CN | 205602350 U | 9/2016 |
| CN | 106163394 A | 11/2016 |
| DE | 29 06 908 A1 | 9/1980 |
| EP | 0 328 415 A1 | 8/1989 |
| EP | 1 384 069 B1 | 6/2006 |
| WO | 2010/143027 A1 | 12/2010 |

* cited by examiner

MOUTHPIECE, SYSTEM AND METHOD FOR ENABLING A MEASUREMENT OF ANALYTES IN EXHALED AIR

This application is a 35 U.S.C. § 371 National Stage Application of PCT/EP2018/064474, filed on Jun. 1, 2018, which claims the benefit of priority to Serial No. DE 10 2017 209 909.7, filed on Jun. 13, 2017 in Germany, the disclosures of which are incorporated herein by reference in their entirety.

BACKGROUND

By means of quantitative measurements of analytes in exhaled air, it is possible to identify and monitor certain respiratory diseases. For example, by determining the concentration of nitric oxide in exhaled air, it is possible to assess the degree of inflammation in the lungs in the case of asthma.

In this connection, determining the concentration of nitric oxide can be carried out using a device disclosed in EP 1384069 B1 via the conversion of nitric oxide into nitrogen dioxide with subsequent measurement of the concentration of nitrogen dioxide with the aid of a field-effect transistor-based gas sensor in the device. The mouthpiece of such a device, via which the user exhales into the device, can be designed as an exchangeable disposable product for reasons of hygiene. Especially when the device is used in medical practices or hospitals, it should be ensured that this does not involve multiple usage of the mouthpiece by different users.

SUMMARY

Against this background, the invention disclosure relates to a mouthpiece for a device for the measurement of analytes in exhaled air. The mouthpiece has a gas path for a conduction of exhaled air to the device. Furthermore, the mouthpiece comprises a film, the film being arranged such that the film blocks the conduction of the exhaled air through the gas path.

A mouthpiece is to be understood to mean especially a part of the device for the measurement of analytes in exhaled air, which part is applied by a user to his lips in order to exhale into the device. In particular, the mouthpiece is a part which is separably connectable to the device. A device for the measurement of analytes in exhaled air is to be understood to mean especially a device comprising a sensor, especially a gas sensor, for the measurement of one or more specified analytes in exhaled air, also called a breath gas analyzer. An analyte can be understood to mean especially a chemical species such as, for example, nitric oxide or nitrogen dioxide. The term analyte can also cover particles or biological entities such as, for example, proteins. Exhaled air can be understood to mean especially air exhaled to the device by a user, also called exhaled gas or breath gas. A gas path in the mouthpiece can be understood to mean especially a conduit for a fluid, especially exhaled air. The gas path is, then, preferably arranged in the mouthpiece such that, in the event of intended application of the mouthpiece to the lips of a user, a quantity of air exhaled by the user can move through the gas path of the mouthpiece to an opening which can be connected to the device. A film can be understood to mean especially a layer or membrane, preferably comprising one or more plastics.

The mouthpiece comprising the gas path-blocking film has the advantage that, before the mouthpiece is used for the first time, the film must be destroyed at least in the gas path-blocking part of the film in order to end the blockade of the gas path and to allow in principle a usage as mouthpiece. Thus, a mouthpiece not yet used as intended can be easily identified as such by a user or by a device for the measurement of analytes in exhaled air, which device has been provided with an appropriately configured sensor, especially a pressure sensor. Thus, an unintended multiple usage of a mouthpiece can be advantageously prevented.

Preferably, the gas path-blocking film is arranged within the mouthpiece, especially in an internal space of the mouthpiece or in the gas path. This has the advantage that the risk of an unintended destruction of the film in the event of an external manipulation of the mouthpiece, for example in the event of an attachment of the mouthpiece to the device, is reduced.

In an advantageous design of the disclosure, the film has a predetermined breaking point. This facilitates the destruction of the film, especially at a well-defined point, for a subsequent intended usage of the mouthpiece. Preferably, the predetermined breaking point is designed, especially on the basis of a thickness and material strength of the film, such that the predetermined breaking point tears when a specified pressure in the gas path of the mouthpiece is exceeded. The specified pressure can preferably be chosen such that a user must overcome a specified resistance when blowing into the mouthpiece. This has the advantage that the user can easily destroy the film in a well-defined manner via the predetermined breaking point for a subsequent measurement. Furthermore, by means of the resistance which is sensible when blowing in and which decreases suddenly when the film tears, the user immediately receives a perceptible feedback about the tearing of the film. Preferably, the predetermined breaking point is arranged in a region of the film that is blocking the gas path. This can advantageously ensure that the blockage of the gas path by the film is ended when the film tears.

According to a further design of the disclosure, the film is fixed, especially adhesively bonded or fused, to a protrusion in the mouthpiece. The protrusion can, for example, be a loop-shaped protrusion, especially an annular or oval protrusion, for example a one-piece formation of a housing of the mouthpiece. This allows a well-defined and easy-to-establish connection of the film to the mouthpiece.

The disclosure also provides a system for the measurement of analytes in exhaled air, wherein the system comprises a mouthpiece according to the disclosure and a device for the measurement of analytes in exhaled air. The mouthpiece is separably connectable to the device. The device comprises a pressure sensor. Preferably, the device further comprises a pump for the pumping of air, especially exhaled air, from the or across the connected mouthpiece. The pump can, then, be configured to suck air from the or across the mouthpiece, especially exhaled air, and/or to pump air beyond the mouthpiece. Furthermore, the device is configured to enable the device for a measurement of specified analytes in the exhaled air when a pressure profile measured via the pressure sensor meets one or more specified conditions. Configuring the device can be understood to mean an arrangement of the pressure sensor and, in particular, a control device, for example a controller, wherein the control device or the controller is configured, especially programmed, such that the control device enables the device for a measurement of specified analytes in the exhaled air when the pressure profile measured via the pressure sensor meets the one or more specified conditions, especially after an evaluation in the control device.

The device of the system according to the disclosure can, for example, be based on a device disclosed in EP 1384069 B1. Preferably, the pressure sensor is arranged in a path of the device, which path is fluidically connected to the gas path of the connected mouthpiece in the event of a destroyed film. If the device comprises the abovementioned pump, the pressure sensor can be arranged in the device and configured such that it can measure over a specified time a pressure prevailing between the pump and the film of the mouthpiece connected to the device. As a result of the specification of conditions in relation to the pressure profile for an enablement of a subsequent measurement, it can be advantageously ascertained whether the film in the mouthpiece is still intact and is blocking the gas path in the mouthpiece. As described above, the film can be advantageously destroyed by a user of the mouthpiece. Alternatively or additionally, the destruction can be achieved by means of a pumping action of the pump. A rapid, sudden pressure change corresponds, then, to a tearing of the film. When the film is torn, there is a comparatively slower pressure change. Thus, the device can advantageously ascertain by itself, preferably by means of an evaluation in the abovementioned control device, whether a mouthpiece not yet used as intended is connected to the device and it can, in this case, enable a usage of the device for a subsequent measurement.

The device of the system according to the disclosure, especially the abovementioned control device, is preferably configured such that one of the specified conditions is met when a specified pressure has been reached in the course of the measured pressure profile. Alternatively, the device or the control device can be configured such that one of the specified conditions is met when a specified pressure profile, a specified pressure gradient or a specified rate of pressure change is ascertained via the pressure sensor. What can be specified in this connection is either a pressure above an ambient pressure, for example above the standard pressure at sea level, or a pressure below an ambient pressure, for example below the standard pressure at sea level, preferably when the pump is configured to pump in the direction of the film or to suck from the direction of the film. For the specified pressure, what is preferably chosen in this connection is a pressure value which is measurably above or below an ambient pressure, for example between 10 and 30 mbar above or below the ambient pressure. Thus, it is advantageously possible to ascertain whether the gas path is blocked and to thus infer a not yet intended use of the mouthpiece.

In a particularly advantageous design of the system according to the disclosure, a pump output of the pump of the device, matched to a specified tear strength of the film of the mouthpiece, is configured to bring about a tearing of the film by means of a suction of fluid, especially air, from a direction of the film of the mouthpiece or by means of a pumping of fluid, especially air, in a direction to the film of the mouthpiece. In the first variant, the pump is configured to suck fluid, especially air, from the direction of the film in order to cause the film to tear. As a result, a negative pressure is generated between the film and the pump. In the second variant, the pump is configured to pump fluid, especially air, in the direction of the film of the mouthpiece in order to cause the film to tear. Instead of a generation of a negative pressure between the pump and the film, what is generated here is a positive pressure between the pump and the film. Both variants have the advantage that the user does not himself need to perform the tearing of the film for an intended use of the system. By contrast, the device can bring about the tearing of the film.

The device, especially the control device, is, then, preferably configured such that the pump is actuated at a specified minimum output for a tearing of the film in the mouthpiece connected to the device. In this connection, the minimum output can preferably be matched to a tear strength of the film in the mouthpiece, meaning that, when the pump is actuated at the minimum output, a tearing of the film is advantageously brought about in an intended use of the system.

In particular, the specified minimum output can be matched to a tear strength of the film, taking into consideration the above-described predetermined breaking point if necessary, via a pressure to be reached.

Preferably, the device can, in this connection, be configured to continuously increase the specified minimum output until the pressure sensor measures a specified pressure change, for example a pressure change between 10 and 30 mbar, especially between 20 and 25 mbar. Such a pressure change occurs after the tearing of the film as a result of the associated pressure equalization, meaning that a successful tearing of the film can be advantageously identified by the device itself, especially via the control device configured for this purpose.

In the abovementioned first variant, the device can, then, preferably be configured to continuously increase the specified minimum output of the pump until the pressure sensor measures a specified pressure drop. Such a pressure drop occurs after the tearing of the film as a result of the associated reduction of the positive pressure prevailing between the film and the pump. In the abovementioned second variant, the device can, then, preferably be configured to continuously increase the specified minimum output until the pressure sensor measures a specified pressure rise. Here, the pressure rise results from a reduction of the negative pressure prevailing between the film and the pump after the tearing of the film. Such a continuous increase in the specified minimum output of the pump has the advantage that films of varying tear strength can be destroyed reliably and there is thus advantageously no need to match the minimum output to a given tear strength of a film.

The disclosure further provides a method for measuring analytes in exhaled air. In a first step, a mouthpiece is connected to a device for the measurement of analytes in exhaled air, the mouthpiece having a gas path for a conduction of exhaled air to the device, the mouthpiece comprising a film, the film being arranged such that it blocks the conduction of the exhaled air through the gas path. In a second step, what takes place is a measurement of a pressure profile by means of a pressure sensor in the device. In a third step, what takes place is an enablement of the device for a measurement of specified analytes in the exhaled air when the measured pressure profile meets one or more specified conditions. Said conditions correspond, in this connection, to an end of the blockade owing to the torn film.

In relation to the advantages of the method according to the disclosure and its further developments below, reference is made to the corresponding abovementioned advantages of the disclosed system according to the disclosure.

In an advantageous further development of the method, a pump of the device is actuated for a tearing of the film. In this connection, the pump is actuated especially for the pumping of exhaled air from the or across the connected mouthpiece.

In a further advantageous further development of the method, one of the specified conditions is met when a specified pressure is reached in the course of the measured pressure profile.

According to an advantageous design of the method, the pump is actuated at a specified minimum output for a tearing of the film in the mouthpiece connected to the device.

Preferably, the specified minimum output is continuously increased until the pressure sensor measures a specified pressure change.

BRIEF DESCRIPTION OF THE DRAWINGS

Exemplary embodiments of the disclosure are schematically depicted in the drawings and are more particularly elucidated in the description which follows. The same reference signs are used for the elements which are depicted in the various figures and have a similar action, in order to dispense with a repeated description of the elements.

What are shown are

DETAILED DESCRIPTION

Figure 1:
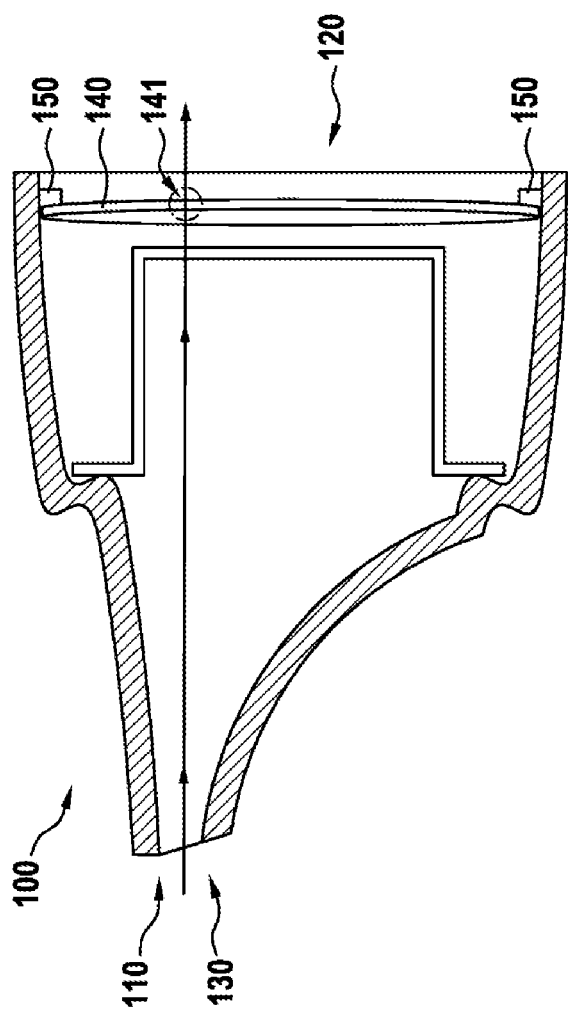
FIG. 1 one exemplary embodiment of the mouthpiece according to the disclosure, FIGS. 2*a, b* one exemplary embodiment of the system according to the disclosure, FIG. 3 a graph of a pressure profile in the case of usage of one exemplary embodiment of the system according to the disclosure, and FIG. 4 one exemplary embodiment of the method according to the disclosure.

FIG. 1 shows one exemplary embodiment of the mouthpiece 100 according to the disclosure for a device for the measurement of analytes in exhaled air, also called a breath gas analyzer. The mouthpiece 100 has a first opening 110 as inlet opening, which can be contacted with a lip of a user for an exhalation into the mouthpiece 100. For example, the first opening 110 is delimited by a part of the mouthpiece 100 which, as shown in FIG. 1, resembles the shape of an end of a beaked flute. The mouthpiece 100 also comprises a second opening 120 which is provided for a connection to the device. Between the first opening 110 and the second opening 120, the mouthpiece 100 comprises a gas path 130 for a conduction of exhaled air to the device. Furthermore, the mouthpiece 100 comprises a film 140, the film 140 being arranged such that it blocks the conduction of the exhaled air through the gas path 130. The film 140 can, for example, be a plastics film, especially containing polyethylene and/or containing polypropylene, which has, for example, a thickness between 0.01 and 0.1 millimeters. By choosing the material and the thickness of the film 140, it is possible to define, depending on the diameter of the gas path 130, how high a positive pressure or negative pressure acting on the film 140 must be in order to cause the film 140 to tear, for example by a user blowing into the opening 110 of the mouthpiece 100. In particular, what can thereby be set is a minimum pressure difference between a first pressure on one side of the film 140 and a second pressure on the other side of the film 140 as a threshold for a tearing of the film. For example, the minimum pressure difference can be between 10 and 25 millibars. The housing of the mouthpiece 100 can likewise be made of plastic.

To facilitate the destruction of the film 140, the film 140 can have a predetermined breaking point 141, for example in the form of a material abrasion for a thinning of the thickness of the film 140 at the site of the predetermined breaking point, in order to ensure a well-defined tear and/or a well-defined minimum pressure. As depicted in FIG. 1, the predetermined breaking point 141 is advantageously arranged in a region of the film 140 that is blocking the gas path 130, meaning that, in the event of a tearing of the film 140, the gas path 130 is no longer blocked by the film 140.

The film 140 can be fixed, for example via an adhesive, to a protrusion 150 of the mouthpiece 100. In this connection, the protrusion 150 can have the shape of a loop encircling the gas path 130, especially the shape of a ring.

Figure 2A:
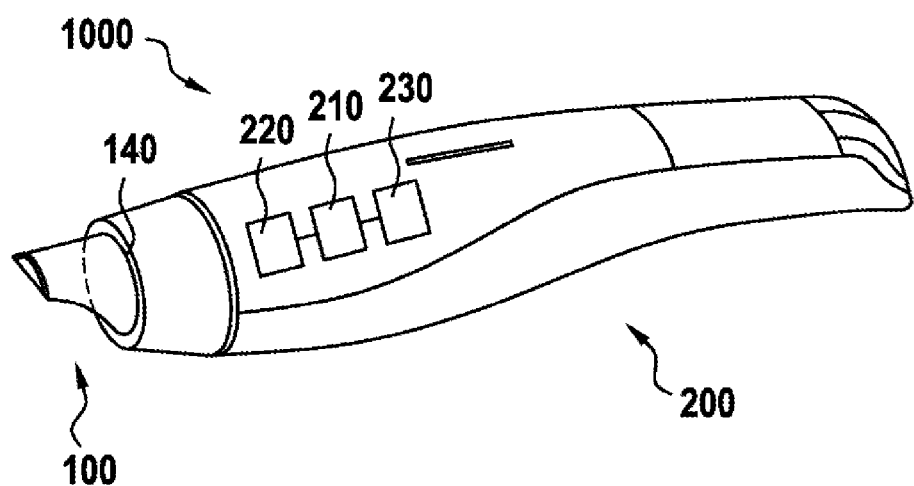

FIG. 2*a* shows one exemplary embodiment of the system 1000 according to the disclosure for the measurement of analytes in exhaled air, comprising one exemplary embodiment of a mouthpiece 100 according to the disclosure and a device 200 for the measurement of analytes in exhaled air. The mouthpiece 100 can, for example, be the above-described embodiment in relation to FIG. 1. The exemplary embodiment of the device 200 can, for example, be based on a device disclosed in EP 1384069 B1.

The mouthpiece 100 is separably connectable to the device 200, for example via a form-fit connection, for example a clip connection. The device 200 comprises a pump 210 for the suction of exhaled air across the connected mouthpiece 100 and a pressure sensor 220. The device 200 is configured, for example via a configuration of a controller 230 in the device 200, to enable the device 200 for a measurement of specified analytes in the exhaled air when a pressure profile measured via the pressure sensor 220 meets one or more specified conditions.

Figure 2B:
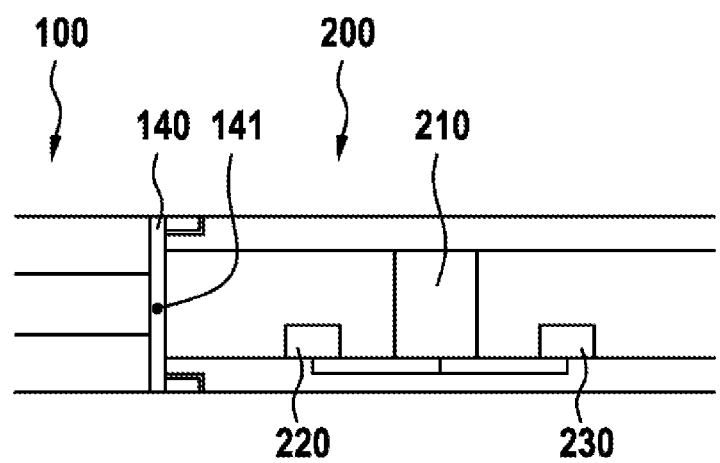

FIG. 2*b* shows a schematic detail of the mouthpiece 100 and the device 200 connected to the mouthpiece 100 in relation to the exemplary embodiment from FIG. 2*a*. As is evident from FIG. 2*b*, the pressure sensor 220 is arranged between the pump 210 and the film 140 of the mouthpiece 100 connected to the device 200 and can thus measure a pressure in the region between film 140 and pump 210. A control device 230, especially a controller 230, is connected to the pressure sensor 220 for a receiving of sensor data and to the pump 210 for an actuation of the pump 210. As explained above, the control device 230 is configured to enable the device 200 for a measurement of specified analytes in the exhaled air when a pressure profile measured via the pressure sensor 220 meets one or more specified conditions. For example, the control device 230 and thus the device 200 can be configured such that one of the specified conditions is met when a specified negative pressure or minimum pressure is reached or fallen short of in the course of the pressure profile measured by the sensor 220. In the case of a connected mouthpiece 100, such a minimum pressure can only be reached when the gas path 130 is blocked. It is thus possible to infer an intact or destroyed film 140.

The pump 230 can also be configured to pump in the direction of the film 140. In this case, the device 200, especially the control device 230, can be configured such that one of the specified conditions is met when a specified positive pressure or maximum pressure is reached or exceeded in the course of the pressure profile measured by the sensor 220. As in the case of a negative pressure generated by the pump 210, such a positive pressure or maximum pressure can only be reached when the gas path 130 is blocked. It is thus possible to infer, in this alternative way, an intact or destroyed film 140.

A tearing of the film 140 can be achieved by means of the user exhaling or blowing into the mouthpiece 100, by means of an actuation of the pump 210 or by means of a combination of the two variants. For example, the control device 230 and thus the device 200 can be configured to actuate the pump 210 at a specified minimum output for a tearing of the film 140. In this connection, the specified minimum output is, depending on the tear strength of the film 140 on the basis of the material, the thickness and optionally the predetermined breaking point 141, set such that a tearing of the film 140 has been achieved when the minimum output is reached on the basis of the associated pump output and the resultant pressure on the film 140. In this connection, the pressure on the film 140 can be brought about by the generation of a negative pressure or a positive pressure in the region between the film 140 and the pump 210.

Figure 3:
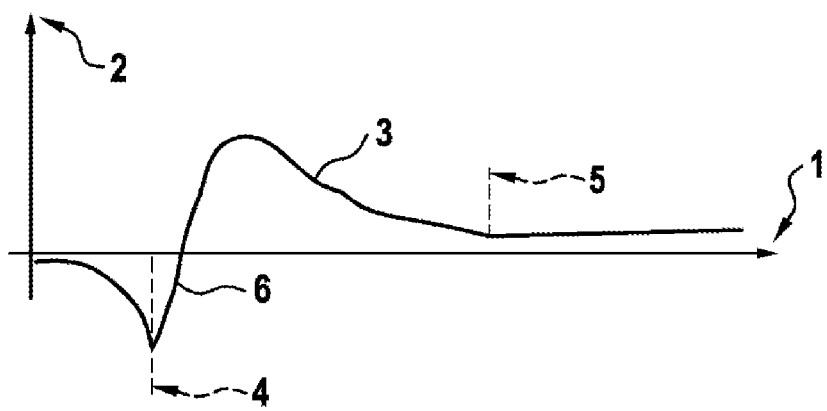

FIG. 3 shows an exemplary pressure profile 3 in the region between the film 140 and the pump 210, as captured by the pressure sensor 220, in the case of a generation of a negative pressure between the film 140 and the pump 210. In this connection, the horizontal axis 1 and the vertical axis 2 of the graph in FIG. 3 respectively show the time and the pressure in the region, in arbitrary units in both cases. At the start of the operation of the pump 210, what is captured by the pressure sensor 220 is a pressure drop up to a first time point 4. At the first time point 4, the film tears and what occurs after a sudden pressure rise 6 is a temporary positive pressure 3 in the region until a comparatively stable pressure in the region is established from the second time point 5. To describe a pressure profile in the case of the generation of a positive pressure between the film 140 and the pump 210, the graph from FIG. 3 must be reflected along the horizontal axis 1.

As an alternative to a fixed specified minimum output, the device 200, especially the control device 230, can be configured such that the specified minimum output is continuously increased until the pressure sensor 220 measures a specified pressure change. As described above and depicted in FIG. 3, what occurs in the case of the generation of a negative pressure between the film 140 and the pump 210 is such a pressure change in the form of a pressure rise 6 after a tearing of the film 140.

Figure 4:
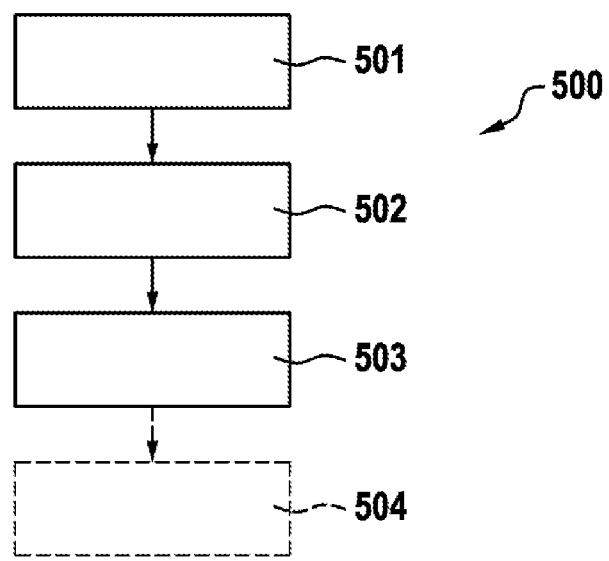

FIG. 4 shows a flowchart in relation to one exemplary embodiment of the method 500 according to the disclosure, for example carried out with a mouthpiece 100 and a device 200 according to the above-described exemplary embodiments. In a first step 501, the mouthpiece 100 is connected to the device 200 for the measurement of analytes in exhaled air, the mouthpiece 100 having a 130 gas path for a conduction of exhaled air to the device and the mouthpiece 100 comprising a film 140, the film 140 being arranged such that it blocks the conduction of the exhaled air through the gas path 130. In a second step 502, a pump 210 of the device 200 is actuated for the pumping of air across the connected mouthpiece 100, especially exhaled air, and a pressure profile is measured by means of a pressure sensor 220 of the device 200. Alternatively or additionally, a user can blow into the opening 110 of the mouthpiece 100 in order to cause the film 140 to tear, preferably supported by the pump 210. In a third step 503, the device 200 is enabled for a measurement of specified analytes in the exhaled air when the measured pressure profile meets one or more specified conditions. In this connection, one of the specified conditions can be met when a specified pressure has been reached in the course of the measured pressure profile. For a tearing of the film 140, the pump 210 can be actuated at a specified minimum output. This can be done in the course of the second step 502 or in a fourth step after an enablement of the device 200 for the measurement. Furthermore, in this connection, the specified minimum output can be continuously increased until the pressure sensor 220 measures a specified pressure rise owing to the tearing of the film 140.

The invention claimed is:

1. A mouthpiece for a device for the measurement of analytes in exhaled air, comprising:
   a body that at least partially defines a gas path for a conduction of exhaled air to the device; and
   a film arranged so as to block the conduction of the exhaled air through the gas path, the film having a predetermined breaking location having a first film thickness that is less than a second film thickness of the remainder of the film.

2. The mouthpiece as claimed in claim 1, wherein the film is arranged within the mouthpiece.

3. The mouthpiece as claimed in claim 2, wherein the film is arranged in an internal space of the mouthpiece or in the gas path.

4. The mouthpiece as claimed in claim 1, wherein the film is fixed to a protrusion that protrudes radially inwardly into the mouthpiece.

5. The mouthpiece as claimed in claim 4, wherein the film is adhesively bonded to the protrusion.

6. The mouthpiece as claimed in claim 1, wherein the predetermined breaking location is in a region of the film that is blocking the gas path.

7. A system for the measurement of analytes in exhaled air, comprising:
   a device including a pressure sensor; and
   a mouthpiece configured to be separably connected to the device, the mouthpiece including:
      a body that at least partially defines a gas path for a conduction of the exhaled air to the device, and
      a film arranged so as to block the conduction of the exhaled air through the gas path,
   wherein the device is configured to be activated for a measurement of specified analytes in the exhaled air when a pressure profile measured via the pressure sensor meets one or more specified conditions.

8. The system as claimed in claim 7, wherein the film has a predetermined breaking location having a first film thickness that is less than a second film thickness of the remainder of the film.

9. The system as claimed in claim 7, wherein the device is configured such that one of the specified conditions is met when a specified pressure has been reached in the course of the measured pressure profile.

10. The system as claimed in claim 7, wherein the device comprises a pump configured to pump air from or across the mouthpiece connected to the device.

11. The system as claimed in claim 10, wherein a pump output of the pump of the device, matched to a specified tear strength of the film of the mouthpiece, is configured to tear the film by (i) a suction of fluid from a direction to the film of the mouthpiece or (ii) a pumping of fluid in a direction to the film of the mouthpiece.

12. The system as claimed in claim 11, wherein the fluid that is sucked or pumped to tear the film includes air.

13. The system as claimed in claim 10, wherein the device is configured such that the pump is actuated at a specified minimum output so as to tear the film in the mouthpiece connected to the device.

14. The system as claimed in claim 13, wherein the device is configured to continuously increase the specified minimum output so as to tear the film until the pressure sensor measures a specified pressure change.

15. A method for enabling a measurement of analytes in exhaled air, comprising:
   connecting a mouthpiece to a device configured to measure analytes in the exhaled air, the mouthpiece including (i) a body that at least partially defines a gas path for a conduction of the exhaled air to the device and (ii)

a film arranged so as to block the conduction of the exhaled air through the gas path;

measuring a pressure profile by a pressure sensor in the device; and activating the device for a measurement of specified analytes in the exhaled air when the measured pressure profile meets one or more specified conditions that correspond to an end of the blocking of the conduction of the exhaled air through the gas path by the film.

16. The method as claimed in claim 15, wherein a pump of the device is actuated to tear the film.

17. The method as claimed in claim 16, wherein the pump is actuated at a specified minimum output so as to tear the film in the mouthpiece connected to the device.

18. The method as claimed in claim 17, wherein the specified minimum output is continuously increased until the pressure sensor measures a specified pressure change.

19. The method as claimed in claim 16, wherein the actuation of the pump to tear the film includes pumping air from or across the mouthpiece connected to the device.

20. The method as claimed in claim 15, wherein one of the specified conditions is met when a specified pressure is reached in the course of the measured pressure profile.

* * * * *